United States Patent [19]
Nakakura et al.

[11] Patent Number: 5,977,109
[45] Date of Patent: Nov. 2, 1999

[54] METHOD FOR STABILIZING COMPOUND DX-52-1 AND LYOPHILIZED COMPOSITION THEREOF

[75] Inventors: Masashi Nakakura, Shizuoka; Eiji Hayakawa; Tokuyuki Kuroda, both of Susono, all of Japan

[73] Assignee: Kyowa Hakko Kogyo Co., Ltd., Tokyo, Japan

[21] Appl. No.: 08/732,384

[22] PCT Filed: Apr. 21, 1995

[86] PCT No.: PCT/JP95/00792

§ 371 Date: Oct. 16, 1996

§ 102(e) Date: Oct. 16, 1996

[87] PCT Pub. No.: WO95/29178

PCT Pub. Date: Nov. 2, 1995

[30] Foreign Application Priority Data

Apr. 25, 1994 [JP] Japan ................................. 6-086337

[51] Int. Cl.[6] .......................... A61K 31/495; A61K 31/50
[52] U.S. Cl. ............................................. 514/250
[58] Field of Search ............................... 514/250

[56] References Cited

U.S. PATENT DOCUMENTS 4,650,869  3/1987  Hirata et al. ............................ 544/343

FOREIGN PATENT DOCUMENTS 0108817   5/1984   European Pat. Off. .
0128370  12/1984   European Pat. Off. .

*Primary Examiner*—Jerome D. Goldberg
*Attorney, Agent, or Firm*—Fitzpatrick, Cella, Harper & Scinto

[57] ABSTRACT

A storage stable dessicated composition is formed of a DX-52-1 derivative according to Formula (I)

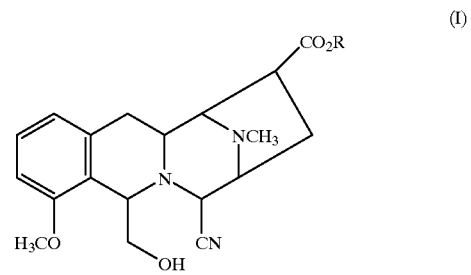

and at least one saccharide. The composition may be formed by lyophilizing a composition which preferably has a pH of 7–12.

12 Claims, No Drawings

METHOD FOR STABILIZING COMPOUND DX-52-1 AND LYOPHILIZED COMPOSITION THEREOF

TECHNICAL FIELD

The present invention relates to a method for stabilizing DX-52-1 and derivatives thereof.

BACKGROUND ART

DX-52-1 according to Formula (I-1) shown below and derivatives thereof are known to have antitumor activity as described in U.S. Pat. No. 4,650,869.

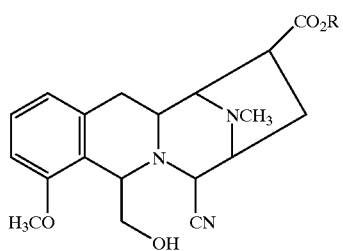

(I-1)

However, DX-52-1 and derivatives thereof (hereinafter, collectively referred to as "DX-52-1 derivatives") decompose easily in an aqueous solution. For example, while DX-52-1 is relatively stable in an aqueous solution under an alkaline condition of pH 7 or above, long-term preservability and stability of DX-52-1 is not sufficient. It is therefore necessary to develop a long-term preservable and stable preparation of DX-52-1.

DISCLOSURE OF THE INVENTION

It is an object of the present invention to overcome these shortcomings of the prior art.

In accordance with an aspect of the present invention, there is provided a method for stabilizing DX-52-1 derivatives represented by Formula (I):

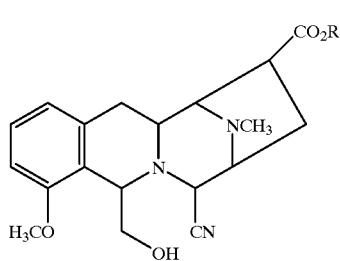

(I)

wherein R is hydrogen or lower alkyl, comprising the steps of preparing a solution containing the DX-52-1 derivative and at least one saccharide, and lyophilizing said solution, said solution having a pH of 7 to 12.

The present invention further relates to a desiccated composition comprising a DX-52-1 derivative according to Formula (I) and at least one saccharide.

The present invention relates to a process for attaining long-term stable compositions of DX-52-1 derivatives according to Formula (I). Preferably, lower alkyl is a straight-chain or branched alkyl group having 1 to 6 carbon atoms. Most preferably, lower alkyl is methyl, ethyl, propyl, isopropyl, butyl, sec-butyl, tert-butyl, pentyl, or hexyl.

The DX-52-1 derivatives represented by Formula (I) can be prepared as disclosed in U.S. Pat. No. 4,650,869. The '869 Patent shows freeze-dried preparations of DX-52-1 which do not contain a saccharide in Example 1 hereinafter.

Suitable DX-52-1 derivatives for use in the present invention are exemplified in Table 1 below.

TABLE 1

| Compound | $^{13}$C-NMR δ (ppm) |
|---|---|
| (DX-52-1) | 183.7, 156.4, 138.1, 129.0, 122.4, 121.4, 119.4, 110.1, 70.8, 65.5, 65.2, 58.7, 58.4, 58.3, 56.3, 45.1, 41.8, 33.0, 30.0 ($D_2O$) |
| | 175.91, 155.83, 136.19, 127.81, 122.05, 120.44, 117.82, 108.59, 70.45, 65.79, 64.70, 58.03, 57.84, 57.60, 55.32, 52.24, 42.77, 41.91, 32.96, 28.91 ($CDCl_3$) |

The present invention is illustrated in detail below.

The DX-52-1 derivative represented by Formula (I) and one or more saccharide are dissolved in a solvent. Preferably, the mixture solution is adjusted to a pH between 7 and 12, typically with an aqueous solution of hydrochloric acid and an aqueous solution of sodium hydroxide. The resulting solution is filtered under a sterile condition through a membrane filter, followed by lyophilization.

Representative examples of the saccharides are lactose, sucrose, raffinose, dextran, mannitol, inositol, galactose, ribose, xylose, mannose, cellobiose, maltose, maltotriose, maltotetraose, and trehalose. Preferably, lactose is used. The saccharide is used in a concentration of 0.005 to 1,000 mg/ml, preferably 1 to 500 mg/ml.

The solvent in which the DX-52-1 derivative and one or more saccharide are dissolved is not particularly limited. Preferable solvents maintain the pH in the range of 7 to 12 as such or permit addition of an aqueous solution of hydrochloric acid and an aqueous solution of sodium hydroxide. In addition to water, preferable examples of the solvents include buffer solutions, such as a citric acid/disodium hydrogenphosphate buffer, a phosphate buffer, a borate buffer, an acetate buffer, and a citrate buffer. These buffer solutions may desirably be used at a concentration of 0.001 to 0.5 M.

If desired, the preparation according to the present invention may also contain pharmaceutically acceptable additives, such as antioxidants, antiseptics, buffering agents, anesthetics, solubilizers, solubilizing auxiliaries, isotonic agents, preservatives, stabilizers, vehicles, binders, disintegrators, wetting agents, lubricants, colorants, aromatics, correctives, coatings, suspending agents, emulsifiers, plasticizers, and surfactants depending on the aim of the preparation. Examples of suitable additives are antioxidants, such as ascorbic acid, vitamin E, butylhydroxytoluene, and benzylhydroxytoluene;

antiseptics, such as p-hydroxybenzoates and chlorobutanol; buffering agents, such as phosphoric acid and citric acid; anesthetics, such as benzyl alcohol and lidocaine; vehicles, such as crystalline cellulose, hydroxypropyl starch, starch, and corn starch; binders, such as Pluran, polyvinyl alcohol, and hydroxypropyl cellulose; disintegrators, such as carboxymethyl cellulose and croscarmellose sodium A; and lubricants, such as magnesium stearate, talc, and hardened oil.

The DX-52-1 derivative is desirably dissolved at a concentration of 0.001 to 1,000 mg/ml, preferably 0.1 to 50 mg/ml. Lyophilization of the solution can be carried out by, for example, preliminary freezing at −50° C. for 5 hours, primary drying at −30° C. and 0.05 mbar for 35 hours and then at 0° C. and 0.05 mbar for 15 hours, and secondary drying at 25° C. and 0.05 mbar for 10 hours.

The thus lyophilized preparation of the DX-52-1 derivative is then sealed for later reconstitution and injection with a rubber stopper and an aluminum cap. In this event, the lyophilized product of the present invention directly provides an injectable solution containing a physiological saccharide, in conformity with Col.3, lines 11–14 of the '869 Patent. Alternatively, the lyophilized preparation may be incorporated into oral dose forms, such as tablets, pills, capsules, and granules; and suppositories. For preparing a pharmaceutical composition for oral or suppository administration, any useful pharmaceutically acceptable carrier can be used. For example, liquid preparations for oral administration such as suspension and syrup can be prepared using water, sugars such as sucrose, sorbitol, and fructose, glycols such as polyethylene glycol and propylene glycol, oils such as sesame oil, olive oil, and soybean oil, preservatives such as p-hydroxybenzoates, flavors such as strawberry flavor and peppermint, and the like. Powders, pills, capsules, and tablets can be prepared using excipients such as lactose, glucose, sucrose, and mannitol, disintegrating agents such as starch and sodium alginate, lubricants such as magnesium stearate and talc, binders such as polyvinyl alcohol, hydroxypropyl cellulose, and gelatin, surfactants such as fatty acid esters, plasticizers such as glycerin, and the like. Tablets and capsules are the most useful oral unit dose forms because of the readiness of administration. For preparing tablets and capsules, solid pharmaceutical carriers are used.

When the preparation containing the DX-52-1 derivative is used as an antitumor agent, the dose and dosage schedule vary depending on such factors as the age, body weight, and conditions of a patient. When administered as an injection, for example, a recommended daily dose is from 0.01 to 50 mg/kg, usually given in a single dose (only one administration or consecutive administration) or at some intervals, for example, 1 to 3 times a week or every three weeks.

BEST MODE FOR CARRYING OUT THE INVENTION

Certain embodiments of the present invention are illustrated by the following Examples, with reference to Comparative Example.

EXAMPLE 1

In 800 ml of distilled water for injection were dissolved 1.0 g of DX-52-1, 50.0 g of lactose, 0.3 g of citric acid monohydrate, and 34.8 g of disodium hydrogenphosphate dodecahydrate. The solution was adjusted to pH 8.0 with 0.1N hydrochloric acid and 0.1N sodium hydroxide, and distilled water for injection was added thereto to make 1000 ml. The solution was charged in 10 ml glass vials in 5 ml portions and lyophilized. Lyophilization of the solution was carried out by preliminary freezing at −50° C. for 5 hours, primary drying at −30° C. and 0.05 mbar for 35 hours and then at 0° C. and 0.05 mbar for 15 hours, and secondary drying at 25° C. and 0.05 mbar for 10 hours. After completion of the lyophilization, the atmosphere was returned to atmospheric pressure in a nitrogen stream, and each vial was sealed with a rubber stopper and an aluminum cap to prepare a lyophilized preparation of DX-52-1.

EXAMPLE 2

In 800 ml of distilled water for injection were dissolved 1.0 g of DX-52-1, 50.0 g of lactose, 0.3 g of citric acid monohydrate, and 34.8 g of disodium hydrogenphosphate dodecahydrate. The solution was adjusted to pH 9.0 with 0.1N hydrochloric acid and 0.1N sodium hydroxide, and distilled water for injection was added thereto to make 1000 ml. The solution was charged in 10 ml glass vials in 5 ml portions and lyophilized. Lyophilization of the solution was carried out by preliminary freezing at −50° C. for 5 hours, primary drying at −30° C. and 0.05 mbar for 35 hours and then at 0° C. and 0.05 mbar for 15 hours, and secondary drying at 25° C. and 0.05 mbar for 10 hours. After completion of the lyophilization, the atmosphere was returned to atmospheric pressure in a nitrogen stream, and each vial was sealed with a rubber stopper and an aluminum cap to prepare a lyophilized preparation of DX-52-1.

Comparative Example 1

In 800 ml of distilled water for injection were dissolved 1.0 g of DX-52-1, 0.3 g of citric acid monohydrate, and 34.8 g of disodium hydrogenphosphate dodecahydrate. The solution was adjusted to pH 8.0 with 0.1N hydrochloric acid and 0.1N sodium hydroxide, and distilled water for injection was added thereto to make 1000 ml. The solution was charged in 10 ml glass vials in 5 ml portions and lyophilized. Lyophilization of the solution was carried out by preliminary freezing at −50° C. for 5 hours, primary drying at −30° C. and 0.05 mbar for 35 hours and then at 0° C. and 0.05 mbar for 15 hours, and secondary drying at 25° C. and 0.05 mbar for 10 hours. After completion of the lyophilization, the atmosphere was returned to atmospheric pressure in a nitrogen stream, and each vial was sealed with a rubber stopper and an aluminum cap to prepare a lyophilized preparation of DX-52-1.

The preservation stability of the lyophilized preparations prepared in Examples 1 and 2 and Comparative Example 1 was evaluated as shown below.

Evaluation

Each of the lyophilized preparations prepared in Examples 1 and 2 and Comparative Example 1 was preserved in a thermostat at 60° C. for 4 weeks. The residual amount of DX-52-1 was analyzed by high performance liquid chromatography (HPLC) under the following condition.

Condition for HPLC Analysis

Column: INERTSIL ODS-2; 4.6×250 mm

Mobile phase: 50 mM phosphate buffer (pH=3.5)/ acetonitrile=82/18 by volume

Flow rate: 1.0 ml/min

Detection wavelength: 220 nm

The results obtained are shown in Table 2 below.

TABLE 2

Preservation Stability of DX-52-1 (60° C. × 4 wks)

| Example No. | Retention of DX-52-1 (%) |
|---|---|
| Example 1 | 98.6 |
| Example 2 | 99.0 |
| Comparative Example 1 | 80.2 |

As is apparent from Table 2, addition of a saccharide results in remarkably improved stability of a lyophilized preparation of DX-52-1.

Industrial Applicability

According to the present invention, there can be provided a method for stabilizing DX-52-1 and derivatives thereof.

We claim:

1. A method for stabilizing a DX-52-1 derivative represented by Formula (I):

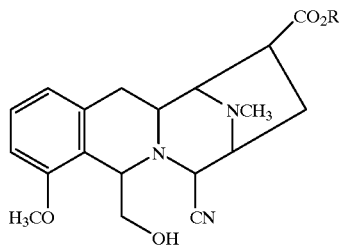

wherein R is hydrogen or lower alkyl, comprising the steps of:
preparing a solution containing from 0.001 to 1,000 mg/ml of the DX-52-1 derivative and from 0.005 to 1,000 mg/ml of at least one saccharide; and
lyophilizing said solution.

2. The method according to claim 1, wherein said solution has a pH of from about 7 to about 12.

3. The method according to claims 1 or 2, wherein R is hydrogen or straight-chain or branched $C_{1-6}$ alkyl.

4. The method according to claim 3, wherein said DX-52-1 derivative is contained in said solution at a concentration of 0.1 to 50 mg/ml.

5. The method according to claim 4, wherein said saccharide is contained in said solution at a concentration of 1 to 500 mg/ml.

6. The method according to claim 5, wherein said solution has a pH of at least about 8.

7. The method according to claim 6, wherein said saccharide is lactose, sucrose, raffinose, dextran, mannitol, inositol, galactose, ribose, xylose, mannose, cellobiose, maltose, maltotriose, maltotetraose, or trehalose.

8. The method according to claim 7, wherein said saccharide is lactose.

9. A desiccated composition, comprising 1–500 parts by weight of a DX-52-1 derivative represented by Formula (I):

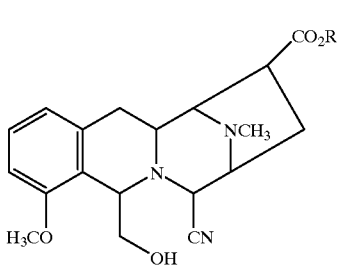

wherein R is hydrogen or lower alkyl, and 10–5,000 parts by weight of at least one saccharide prepared by the process of claim 1.

10. The composition according to claim 9, wherein R is hydrogen or straight-chain or branched $C_{1-6}$ alkyl and said saccharide is lactose, sucrose, raffinose, dextran, mannitol, inositol, galactose, ribose, xylose, mannose, cellobiose, maltose, maltotriose, maltotetraose, or trehalose.

11. The composition according to claim 10, wherein said saccharide is lactose.

12. A suppository or oral dose form of the composition according to claim 9, 10, or 11, further comprising a pharmaceutically acceptable carrier.

* * * * *